United States Patent [19]

Fifolt et al.

[11] Patent Number: 4,521,616
[45] Date of Patent: * Jun. 4, 1985

[54] METHOD FOR THE PREPARATION OF FLUOROANTHRANILIC ACIDS

[75] Inventors: Michael J. Fifolt, Grand Island, N.Y.; Arthur M. Foster, Birmingham, Mich.

[73] Assignee: Occidental Chemical Corporation, Niagara Falls, N.Y.

[*] Notice: The portion of the term of this patent subsequent to Feb. 15, 2000 has been disclaimed.

[21] Appl. No.: 220,574

[22] Filed: Dec. 29, 1980

[51] Int. Cl.³ .............................................. C07C 101/42
[52] U.S. Cl. .................................... 562/456; 562/442
[58] Field of Search ................................ 562/456, 442

[56] References Cited

U.S. PATENT DOCUMENTS

| 1,991,790 | 2/1935 | Cook et al. | 562/442 |
| 2,275,006 | 3/1942 | Bindler | 562/442 |
| 3,014,033 | 12/1961 | Havant et al. | 562/442 |
| 4,276,433 | 6/1981 | Kilpper et al. | 562/458 |
| 4,374,266 | 2/1983 | Fifolt | 562/456 |
| 4,374,267 | 2/1983 | Fifolt | 562/456 |

FOREIGN PATENT DOCUMENTS

| 2328757 | 1/1975 | Fed. Rep. of Germany | 562/456 |
| 1436810 | 5/1974 | United Kingdom | 562/456 |

OTHER PUBLICATIONS

Singh et al., J. Ind. Chem. Soc., vol. 55, pp. 928–931, (1978).
Kilpper et al., Chem. Abst., vol. 92, #76126r, (1980).
Singh, Chem. Abst., vol. 90, #137754b, (1979).
Azuma et al., Chem. Abst., vol. 97, #141417t, (1972).
Panneitz, Chem. Abst., vol. 92, #60321q, (1980).

*Primary Examiner*—James H. Reamer
*Attorney, Agent, or Firm*—James F. Tao; Arthur S. Cookfair

[57] ABSTRACT

A process for the preparation of fluoroanthranilic acid compounds comprises
(A) reacting ammonium fluorophthalamate or a fluorophthalamic acid of the formula

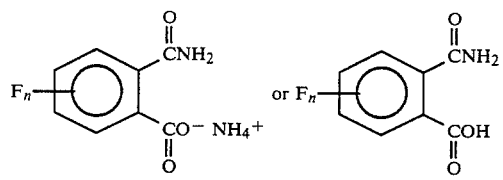

where n is 1 or 2, with an alkali or alkaline earth metal hypochlorite to form the corresponding fluoroanthranilic acid of the formula

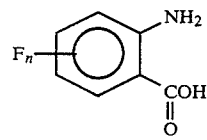

where n is as previously defined.

23 Claims, No Drawings

METHOD FOR THE PREPARATION OF FLUOROANTHRANILIC ACIDS

BACKGROUND OF THE INVENTION

This invention relates to a process for the preparation of fluorinated aromatic compounds and in particular to a process for the preparation of fluoro-anthranilic acids. The fluoroanthranilic acids are useful as chemical intermediates for the preparation of fluoroanilines and for the further preparation of various dyestuffs, pesticides, and pharmaceuticals.

SUMMARY OF THE INVENTION

In accordance with this invention there is provided a process for the preparation of fluoroanthranilic acid compounds comprising (A) reacting an ammonium fluorophthalamate or a fluorophthalamic acid of the formula

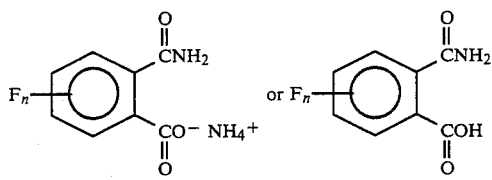

where n is 1 or 2, with an alkali or alkaline earth metal hypochlorite to form a fluoroanthranilic acid of the formula

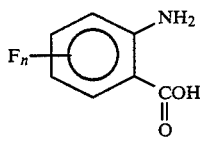

where n is as previously defined.

The fluoroanthranilic acids are useful intermediates in the preparation of various other fluorinated aromatic compounds. For example the fluoroanthranilic acid may be reacted in an acidic medium such as hydrochloric acid with sodium nitrite to prepare fluorobenzoic acids.

The ammonium fluorophthalamates utilized in the process of this invention are a novel class of compounds represented by the formula

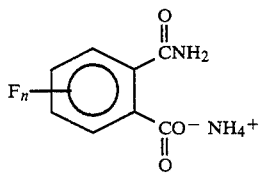

where n is 1 or 2.

The compounds are prepared by the reaction of an chlorophthalic anhydride with potassium or cesium fluoride to form a corresponding fluorophthalic anhydride and subsequent ammonolysis of the fluorophthalic anhydride. Details for the preparation of the ammonium fluorophthalamates are disclosed in co-pending application, now U.S. Pat. No. 4,374,266, the disclosure of which is hereby incorporated by reference.

The fluorophthalamic acids utilized in the process of this invention are a novel class of compounds characterized by the formula

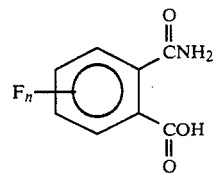

where n is 1 or 2.

The compounds are prepared by acidification of ammonium fluorophthalamates. Details regarding the preparation of the fluorophthalamic acids are disclosed in co-pending application, now U.S. Pat. No. 4,374,267, the disclosure of which is hereby incorporated by reference.

The preparation of fluoroanthranilic acids (step A) by reaction of an ammonium fluorophthalamate or a fluorophthalamic acid with an alkali, or alkali earth metal hypochlorite, preferably sodium hypochlorite, may be carried out over a wide range of temperatures, typically between about 40° and about 100°, and most preferably between about 60° and about 80° Celsius. It has further been found advantageous to add the alkaline or alkaline earth metal hypochlorite in combination with a strong base such as an alkali metal or alkali earth metal hydroxide, preferably sodium hydroxide. It has been found that this preferred reaction scheme, is of benefit in minimizing the formation of undesired by-products. In a preferred method the fluoroanthranilic acids are prepared by reacting an ammonium fluorophthalamate with about 0.5 to 5.0 moles, preferably about 1.0 to about 1.5 moles of alkali or alkaline earth metal hydroxide and about 1.0 to about 5.0 preferably about 1.0 to about 1.5 moles of an alkali or alkaline earth metal hypochlorite. It is preferred to carry out the reaction at about atmospheric pressure, however, subatmospheric or superatmospheric pressures may be employed, if desired.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

(A) To a solution of 0.18 parts of sodium hydroxide in 5.0 parts of water was added 0.5 parts of 4,5-difluorophthalamic acid. The solution was heated to about 50° C. and 3.5 parts of 5.7% sodium hypochlorite solution was added. The reaction solution was heated to about 65°–70° C. and maintained at that temperature range for about 30 minutes then cooled to about 20°–25° C. Concentrated hydrochloric acid was slowly added with the resultant formation of a precipitate. The addition of hydrochloric acid was continued until no further precipitate formed. The mixture was then extracted with chloroform, dried over anhydrous sodium sulfate, filtered, and the remaining chloroform removed under reduced pressure to yield 0.42 parts of 4,5-difluoroanthranilic acid having a melting point of 182°–183° C. The product was analyzed by infra-red spectrographic techniques and liquid phase chromatographic techniques and confirmed to be a high purity (99.0%) 4,5-difluoroanthranilic acid in a yield of 99% based on the starting 4,5-difluorophthalamic acid.

(B) A solution of 0.8 parts of 4,5-difluoroanthranilic acid in 40 parts of 1N sulfuric acid was placed in a reaction vessel equipped with a reflux condenser. The reaction solution was refluxed for 70 hours, then cooled, basified to a pH of about 8.0–9.0 by addition of 1N sodium hydroxide, saturated with sodium chloride and extracted with diethyl ether. The mixture was then dried over anhydrous sodium sulfate, filtered, and the diethyl ether removed under reduced pressure to yield 0.54 parts of product. Chromatographic analysis of the product indicated a 78% yield (based on the 4,5-difluoroanthranilic acid) of 96% pure 3,4-difluoroaniline. The structure of the 3,4-difluoroaniline product was confirmed by $C^{13}$ NMR.

EXAMPLE 2

(A) Dimethoxyethane (43 parts) was charged to a reactor and ammonia was bubbled in to form a saturated solution. The ammonia addition was maintained while a solution of 1.84 parts of 4,5-difluorophthalic anhydride in 13 parts of dimethoxyethane was added slowly over a period of 0.5 hours. The reaction mixture was stirred for an additional 5 minute period and the dimethoxyethane was removed by vacuum distillation. The remaining white solid (the ammonium salt of 4,5-difluorophthalamic acid) was dissolved in 20 parts of aqueous sodium hydroxide (40% NaOH) and the solution was de-gassed under moderately reduced pressure to remove any remaining ammonia; then heated at atmospheric pressure, to 50° C. and maintained at that temperature while 14.1 parts of a 5.78% aqueous sodium hypochlorite solution was added. The solution was then heated to 60°–65° C. and maintained at that temperature, with stirring for about 30 minutes; then cooled to about 20°–25° C. and acidified to a pH of 4–6, by addition of concentrated hydrochloric acid. A precipitate formed and the mixture was extracted with chloroform. The acidification procedure was repeated until no additional precipitate formed. The combined extracts were dried over anhydrous sodium sulfate, filtered, and the chloroform removed by vacuum distillation to yield 1.34 parts of solid 4,5-difluoroanthranilic acid having a melting point of 180°–181° C. The chemical structure of the product was confirmed by infrared analysis.

(B) Following the procedure of Example 1B, the 4,5-difluoroanthranilic acid was decarboxylated by reaction with sulfuric acid, to form 3,4-difluoroaniline.

EXAMPLE 3

(A) A mixture of 20 parts of 3-chlorophthalic anhydride, and 20 parts of anhydrous potassium fluoride was heated and maintained at about 235° C. for about 9 hours. The reaction mixture was then cooled and the crude product removed by vacuum distillation and recrystallized from chloroform to yield 12.65 parts of purified 3-fluorophthalic anhydride (69% yield).

(B). Ten parts of the 3-fluorophthalic anhydride was dissolved in 78.3 parts of acetonitrile and ammonia was bubbled into the solution until no 3-fluorophthalic anhydride could be detected (by thin layer chromatography on silica gel with a 7:2:1 mixture of toluene:ethyl acetate:acetic acid). The acetonitrile was then removed under reduced pressure to yield 14.8 parts of white solid - a mixture of the ammonium salts of 3- and 6-fluorophthalamic acid.

(C) The mixture of 3- and 6-fluoro ammonium phthalamate salts (14.8 parts) prepared as in 3C, above, was dissolved in 140 parts of a solution of 0.77M NaOCl and 1.5M NaOH. The solution was heated and maintained at 80° C. for about 30 minutes, then cooled to about 25° C. and acidified by addition of concentrated hydrochloric acid. An orange precipitate formed, which was extracted with chloroform (3 times) dried over anhydrous sodium sulfate and filtered. The chloroform was removed under reduced pressure leaving 6.9 parts of orange solid having a melting point range of 160°–177° C. The product was analyzed by $C^{13}$ nuclear magnetic resonance techniques and found to be a mixture of 3-fluoroanthranilic acid: 6-fluoroanthranilic acid: three unknowns of 68:20:9:2:1. The 3-fluoroanthranilic acid and 6-fluoroanthranilic acids were separated by recrystallization from chloroform and chromatographic treatment of the mother liquors, using silica gel with chloroform as a solvent. Recrystallization from chloroform, yielded 3.3 parts of 3-fluoroanthranilic acid having a melting point of 181°–182.5° C. and 0.21 parts of 6-fluoroanthranilic acid having a melting point of 168°–169° C.

EXAMPLE 4

A solution of 18 parts of sodium hydroxide and 40 parts of ammonium salt of 3-fluorophthalamic acid was heated to 50° C. and 325 parts of aqueous 5.5% sodium hypochlorite solution was added. The solution was heated and maintained at about 65°–70° C. for 30 minutes, then cooled to about 25° C. and acidified by addition of concentrated hydrochloric acid. As the solution was acidified an orange precipitate formed which was extracted with chloroform. The acidification-extraction procedure was repeated until no further precipitate formed during acidification. The chloroform extracts were combined, dried over anhydrous sodium sulfate, filtered, and the chloroform removed under reduced pressure, yielding 35 parts of 3-fluoroanthranilic acid.

What is claimed is:

1. A process for the preparation of fluoroanthranilic acids comprises reacting ammonium fluorophthalamate or a fluorophthalamic acid of the formula

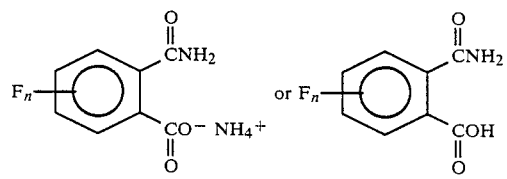

where n is 1 or 2 with an alkali metal or alkali earth metal hypochlorite to form a fluoroanthranilic acid.

2. A process according to claim 1 comprising reacting an ammonium fluorophthalamate of the formula

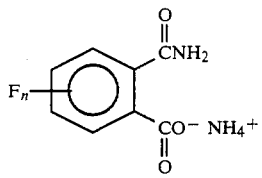

where n is 1 or 2 with an alkali or alkali earth metal hypochlorite.

3. A process according to claim 2 wherein the ammonium fluorophthalamate is a difluorophthalamate of the formula

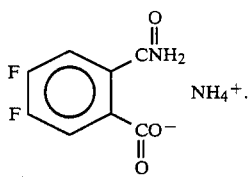

4. A process according to claim 2 wherein n is 1.
5. A process according to claim 2 wherein n is 2.
6. A process according to claim 2 wherein the hypochlorite is an alkali metal hypochlorite.
7. A process according to claim 6 wherein the hypochlorite is sodium hypochlorite.
8. A process according to claim 2 which comprises reacting an ammonium difluorophthalamate of the formula

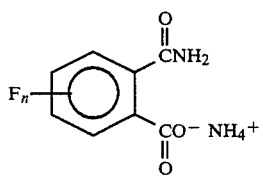

where n is 1 or 2 with a basic reaction medium comprising an alkali or alkali earth metal hydroxide in combination with an alkali or alkali earth metal hypochlorite.

9. A process according to claim 8 wherein the basic reaction medium comprises sodium hydroxide and sodium hypochlorite.

10. A process according to claim 9 wherein 4,5-difluoroanthranilic acid is prepared by reacting ammonium 4,5-difluorophthalamate with a basic reaction medium comprising sodium hydroxide and sodium hypochlorite.

11. A process according to claim 9 wherein 3-fluoroanthranilic acid is prepared by reacting ammonium 3-fluorophthalamate with a base reaction medium comprising sodium hydroxide and sodium hypochlorite.

12. A process according to claim 9 wherein 6-fluoroanthranilic acid is prepared by reacting ammonium 6-fluorophthalamate with a basic reaction medium comprising sodium hydroxide and sodium hypochlorite.

13. A process according to claim 1 comprising reacting a fluorophthalamic acid of the formula

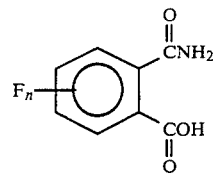

where n is 1 or 2 with an alkali or alkali earth metal hypochlorite.

14. A process according to claim 13 wherein the fluorophthalamic acid is a difluorophthalamic acid of the formula

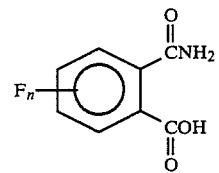

15. A process according to claim 13 wherein n is 1.
16. A process according to claim 13 wherein n is 2.
17. A process according to claim 13 wherein the hypochlorite is an alkali metal hypochlorite.
18. A process according to claim 17 wherein the hypochlorite is sodium hypochlorite.
19. A process according to claim 13 which comprises reacting an difluorophthalamic acid of the formula

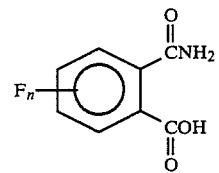

where n is 1 or 2 with a basic reaction medium comprising an alkali or alkali earth metal hydroxide in combination with an alkali or alkali earth metal hypochlorite.

20. A process according to claim 19 wherein the basic reaction medium comprises sodium hydroxide and sodium hypochlorite.

21. A process according to claim 20 wherein 4,5-difluoroanthranilic acid is prepared by reacting 4,5-difluorophthalamic acid with a basic reaction medium comprising sodium hydroxide and sodium hypochlorite.

22. A process according to claim 20 wherein 3-fluoroanthranilic acid is prepared by reacting 3-fluorophthalamic acid with a base reaction medium comprising sodium hydroxide and sodium hypochlorite.

23. A process according to claim 20 wherein 6-fluoroanthranilic acid is prepared by reacting 6-fluorophthalamic acid with a basic reaction medium comprising sodium hydroxide and sodium hypochlorite.

* * * * *